United States Patent
Jeon et al.

(10) Patent No.: US 10,533,952 B2
(45) Date of Patent: Jan. 14, 2020

(54) METHOD OF INSPECTING A TERMINAL OF A COMPONENT MOUNTED ON A SUBSTRATE AND SUBSTRATE INSPECTION APPARATUS

(71) Applicant: KOH YOUNG TECHNOLOGY INC., Seoul (KR)

(72) Inventors: Kye-Hoon Jeon, Seoul (KR); Dal-An Kwon, Hwaseong-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 212 days.

(21) Appl. No.: 15/534,130

(22) PCT Filed: Dec. 8, 2015

(86) PCT No.: PCT/KR2015/013397
§ 371 (c)(1),
(2) Date: Jun. 8, 2017

(87) PCT Pub. No.: WO2016/093597
PCT Pub. Date: Jun. 16, 2016

(65) Prior Publication Data
US 2019/0094151 A1 Mar. 28, 2019

(30) Foreign Application Priority Data
Dec. 8, 2014 (KR) .................. 10-2014-0174895
Dec. 8, 2015 (KR) .................. 10-2015-0174149

(51) Int. Cl.
*G01N 21/88* (2006.01)
*G06T 7/00* (2017.01)
(Continued)

(52) U.S. Cl.
CPC ....... *G01N 21/8806* (2013.01); *G01N 21/956* (2013.01); *G06T 7/0004* (2013.01);
(Continued)

(58) Field of Classification Search
CPC ............. G01N 21/8806; G01N 21/956; G01N 2021/8845; G01N 2021/95646;
(Continued)

(56) References Cited

U.S. PATENT DOCUMENTS

| 7,019,826 B2 * | 3/2006 | Vook ................. G06T 7/0002 250/559.34 |
| 8,508,591 B2 * | 8/2013 | Sones ................. G06T 7/571 348/135 |

(Continued)

FOREIGN PATENT DOCUMENTS

| CN | 101943571 | 1/2011 |
| DE | 10 2013 206 927 | 10/2013 |

(Continued)

OTHER PUBLICATIONS

International Search Report for International Application No. PCT/KR2015/013397, dated Apr. 7, 2016.
(Continued)

*Primary Examiner* — Jonathan S Lee
(74) *Attorney, Agent, or Firm* — Kile Park Reed & Houtteman PLLC (57) ABSTRACT

A substrate inspection apparatus according to an embodiment of the present invention comprises a projection unit, an illumination unit, an image acquisition unit and a processing unit. The projection unit irradiates an inspection target with light for obtaining three-dimensional shape information of the inspection target. The illumination unit irradiates the inspection target with at least two lights having different colors. The image acquisition unit acquires a first image by receiving light irradiated by the projection unit and reflected from the inspection target, and a second image by receiving the lights irradiated by the illumination unit and reflected from the inspection target. The processing unit acquires brightness information and color information from the first
(Continued)

image and the second image, respectively, which are acquired by the image acquisition unit, and acquires at least a portion of a boundary by using the bright information and the color information. Therefore, the accuracy and reliability of the inspection can be improved.

14 Claims, 8 Drawing Sheets

(51) Int. Cl.
    *G06T 7/174*     (2017.01)
    *G06T 7/521*     (2017.01)
    *G06T 7/13*     (2017.01)
    *G06T 7/90*     (2017.01)
    *G01N 21/956*     (2006.01)

(52) U.S. Cl.
    CPC ............... *G06T 7/13* (2017.01); *G06T 7/174* (2017.01); *G06T 7/521* (2017.01); *G06T 7/90* (2017.01); *G01N 2021/8845* (2013.01); *G01N 2021/95646* (2013.01); *G06T 2207/10024* (2013.01); *G06T 2207/10028* (2013.01); *G06T 2207/10152* (2013.01); *G06T 2207/20221* (2013.01); *G06T 2207/30141* (2013.01)

(58) Field of Classification Search
    CPC .......... G06T 7/521; G06T 7/13; G06T 7/174; G06T 7/90; G06T 7/0004; G06T 2207/10024; G06T 2207/10028; G06T 2207/10152; G06T 2207/20221; G06T 2207/30141
    USPC ......................................................... 382/147
    See application file for complete search history.

(56) References Cited

U.S. PATENT DOCUMENTS

| | | | |
|---|---|---|---|
| 9,091,725 B2* | 7/2015 | Jeong | G01B 11/2531 |
| 2001/0012393 A1* | 8/2001 | Yonezawa | G01N 21/8803 |
| | | | 382/145 |
| 2010/0290696 A1 | 11/2010 | Jeong et al. | |
| 2011/0002527 A1 | 1/2011 | Jeong et al. | |
| 2011/0255771 A1 | 10/2011 | Kwon | |
| 2012/0128232 A1 | 5/2012 | Jeong | |
| 2014/0132953 A1 | 5/2014 | Jeong | |

FOREIGN PATENT DOCUMENTS

| | | |
|---|---|---|
| KR | 10-2009-0092116 | 8/2009 |
| KR | 10-2009-0120394 | 11/2009 |
| KR | 10-2010-0012558 | 2/2010 |
| KR | 10-2011-0089486 | 8/2011 |
| KR | 10-2012-0090926 | 8/2012 |

OTHER PUBLICATIONS

Written Opinion for International Application No. PCT/KR2015/013397 with English translations, dated Apr. 7, 2016.

* cited by examiner

METHOD OF INSPECTING A TERMINAL OF A COMPONENT MOUNTED ON A SUBSTRATE AND SUBSTRATE INSPECTION APPARATUS

TECHNICAL FIELD

The present invention relates to a method of inspecting a terminal of a component, and more particularly to a method of inspecting a terminal of a component mounted on a substrate.

BACKGROUND ART

In general, at least one printed circuit board (PCB) is provided in an electronic device, and various circuit components such as a circuit pattern, a connection pad portion, and a driving chip electrically connected to the connection pad portion are mounted on the PCB.

These components are mounted in such a way that the terminals of each component are soldered to the pads of the PCB, and the components need to be inspected whether the components are properly soldered to the PCB or not. In these inspection, it is important to clearly distinguish between the terminal area and the solder area of the component in order to increase the accuracy of the inspection. It is important to find the border of the terminal area of the component, for example the terminal end of the component, in order to clearly distinguish the areas.

Conventionally, a method of finding a terminal end of a component in a two-dimensional image, a method of finding a terminal end by performing rectangle fitting after binarizing a height above a reference height as a threshold value after measuring a height value, etc., have been adopted.

However, there is a problem of highly diffused reflection at the terminal end and a problem of existing inspection noise, so that measurement accuracy and reliability are lowered. In addition, when the size of a component is small, such as a component mounted on a notebook computer, a smart pad, or a mobile phone, the error becomes greater since the size of the component is very small compared to the size of the pixel according to the resolution of the camera.

DETAILED DESCRIPTION OF THE INVENTION

Objects of the Invention

Accordingly, it is an object of the present invention to provide a method of inspecting a terminal of a component, which can accurately set a boundary of a terminal of the component mounted on a substrate.

Another object of the present invention is to provide a substrate inspection apparatus, which can accurately set a boundary of a terminal of the component mounted on a substrate.

Technical Solution

A method of inspecting a terminal of a component, according to an embodiment of the present invention, comprises acquiring a first image by irradiating an inspection target with light for obtaining three-dimensional image of the inspection target and receiving the light reflected by the inspection target, and a second image by irradiating the inspection target with at least two lights with different colors and receiving the at least two lights reflected by the inspection target, acquiring brightness information from the first image, and color information from the second image, and acquiring at least a portion of a boundary of the terminal of the inspection target by using the brightness information and the color information.

In one embodiment, acquiring brightness information from the first image, and color information from the second image, may comprise combining the first image and the second image to produce a composite image, and acquiring the brightness information and the color information from the composite image.

In one embodiment, the light for obtaining three-dimensional image of the inspection target may be irradiated with a first inclination angle with reference to a normal line perpendicular to the plane of the inspection target, and the at least two lights with different colors may include at least a first color light and a second color light having a different color from the first color light. The first color light may be irradiated with a second inclination angle smaller than the first inclination angle, and the second color light may be irradiated with a third inclination angle larger than the first inclination angle.

Acquiring at least a portion of a boundary of the terminal of the inspection target by using the brightness information and the color information, may comprise setting an inspection area including a terminal of the inspection target in a composite image of the first and second images, setting a section in which the color of a pixel changes from the first color to another color along a direction from one side boundary of the terminal to other side boundary (hereinafter referred to as 'reference direction') within the inspection area, detecting a change in color information per pixel and a change in brightness information per pixel in the section, and obtaining at least a portion of the boundaries of the terminal, based on the change of the color information per pixel and the change of the brightness information per pixel.

The color and the brightness may be set to a normalized quantitative value for each pixel, and the change of the color and the change of the brightness may be respectively a change of a color value per pixel and a change of a brightness value per pixel according to the reference direction.

For example, the first color may be red. The change of the color may be increased in the section according to the reference direction and the change of the brightness may be decreased in the section according to the reference direction. The boundary of the terminal may be determined by a point where an increasing trend line corresponding to the change of the color value per pixel meets a decreasing trend line corresponding to the change of the brightness value per pixel.

The method may further comprise obtaining height data from the first image, and modifying the brightness information by using the height data. In this case, acquiring at least a portion of a boundary of the terminal of the inspection target, may be performed by using the modified brightness information and the color information. In one embodiment, modifying the brightness information by using the height data may be performed by setting the brightness information to zero when the height data is less than or equal to a reference height.

A substrate inspection apparatus according to an embodiment of the present invention comprises a projection unit, an illumination unit, an image acquisition unit and a processing unit. The projection unit irradiates an inspection target with light for obtaining three-dimensional shape information of the inspection target. The illumination unit irradiates the inspection target with at least two lights having different colors. The image acquisition unit acquires a first image by receiving light irradiated by the projection unit and reflected from the inspection target, and a second image by receiving the lights irradiated by the illumination unit and reflected from the inspection target. The processing unit acquires brightness information and color information from the first image and the second image, respectively, which are acquired by the image acquisition unit, and acquires at least a portion of a boundary by using the bright information and the color information.

In one embodiment, the processing unit may combine the first image and the second image to generate a composite image, and may acquire the brightness information and the color information from the composite image.

In one embodiment, at least one projection unit may be disposed, and irradiate the inspection target with light for obtaining three-dimensional shape information with a first inclination angle with respect to a normal line perpendicular to a plane of the inspection target. The lighting unit may comprise a first illumination unit irradiating the inspection target with a first color light having a first color with a second inclination angle smaller than the first inclination angle of the projection unit, and a second illumination unit irradiating the inspection target with a second color light having a second color different from the first color with a third inclination angle larger than the first inclination angle of the projection unit.

For example, the processing unit may set a section in which the color of a pixel changes from the first color to another color along a direction from one side boundary of the terminal to other side boundary (hereinafter referred to as 'reference direction') within an inspection area in the composite image of the first and second images, which includes the terminal of the inspection target, and may acquire at least a portion of a boundary of the terminal, based on a change of the color information per pixel and a change of the brightness information per pixel in the section.

In one embodiment, the color and the brightness may be set to a normalized quantitative value for each pixel, and the change of the color and the change of the brightness may be respectively a change of a color value per pixel and a change of a brightness value per pixel according to the reference direction.

For example, the first color may be red. The change of the color may be increased in the section according to the reference direction and the change of the brightness may be decreased in the section according to the reference direction. The boundary of the terminal may be determined by a point where an increasing trend line corresponding to the change of the color value per pixel meets a decreasing trend line corresponding to the change of the brightness value per pixel.

In one embodiment, the processing unit may acquire height data from the first image, modify the brightness information by using the height data, and acquire at least a portion of the boundaries of the terminal of the inspection target by using the modified brightness information and the color information. The processing unit may set the brightness information to zero, when the height data is less than or equal to a reference height in modifying the brightness data by using the height data.

Advantageous Effects

According to the method of inspecting a terminal of a component and the substrate inspection apparatus described above, a boundary of a terminal of the inspection target is acquired by using the bright information and the color information respectively obtained from the image for measuring three-dimensional shape and the color image to secure high accuracy and reliability, thereby improving the accuracy and reliability of inspection.

In addition, the terminal boundary of the inspection target can be obtained from data obtained by quantifying the brightness information and the color information pixel by pixel, the terminal boundary of the component can be detected in sub-pixel unit by determining the terminal end as an intersection of the graph obtained according to the change of the color value of each pixel, and the graph obtained according to the change of the brightness of each pixel, and the boundary of the terminal of the component can be obtained more accurately even when the size of the parts is small.

In addition, not only can three-dimensional shape information be acquired from an image for acquiring three-dimensional shape information of an inspection target, but also utilized for extraction of brightness information, efficient data utilization can be achieved.

MODE FOR INVENTION

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art.

It will be understood that, although the terms first, second, third etc. may be used herein to describe various elements, components, regions, layers and/or sections, these elements, components, and/or sections should not be limited by these terms. These terms are only used to distinguish one element, component, region, layer or section from another region, layer or section. Thus, a first element, component, or section discussed below could be termed a second element, component, or section without departing from the teachings of the present invention.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, preferred embodiments of the present invention will be described in detail with reference to the drawings.

Figure 1:
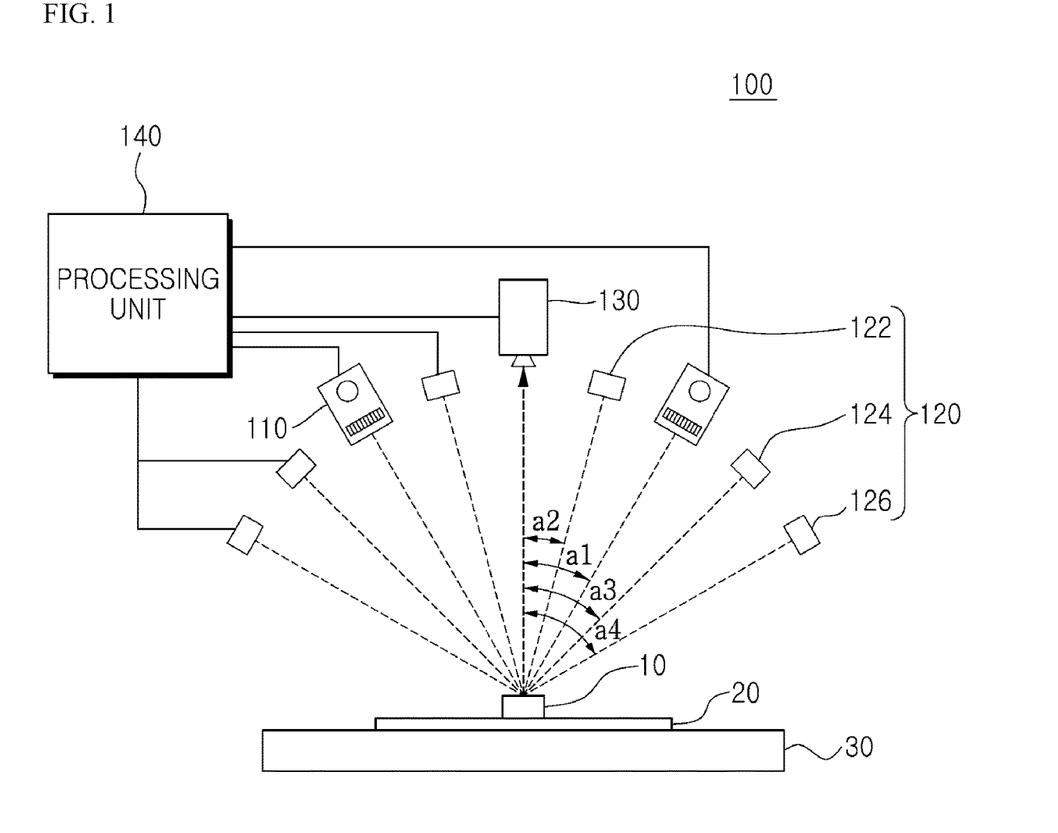
FIG. 1 is a conceptual diagram showing a substrate inspection apparatus according to an embodiment of the present invention.

FIG. 1 is a conceptual diagram showing a substrate inspection apparatus according to an embodiment of the present invention.

Referring to FIG. 1, a substrate inspection apparatus 100 according to an exemplary embodiment of the present invention may include a projection unit 110, an illumination unit 120, an image acquisition unit 130 and a processing unit 140. The substrate inspection apparatus 100 may be provided for inspection of a terminal of an inspection target 10 such as a component, which is to be inspected. At this time, the terminal of the inspection target 10 means one end of the component, and may be one or plural.

The projection unit 110 irradiates the inspection target 10 with light for acquiring the three-dimensional shape information of the inspection target 10.

The inspection target 10 may include a component mounted on the substrate 20. The substrate 20 may be disposed on a stage 30.

In one embodiment, the projection unit 110 may irradiate the inspection target 10 with a grid pattern light n-times, while phase-shifting the grid pattern light n-times by using a grid transfer device or a liquid crystal display to irradiate the phase-shifted grid pattern light. The image acquisition unit 130 to be described below may obtain a grid pattern image according to the grid pattern light.

The projection unit 110 may irradiate the light in a direction perpendicular to the plane of the inspection target 10, or in a direction oblique with respect to a normal line perpendicular to the plane, for example in a direction oblique with respect to the normal line by a first inclination angle a1 as shown in FIG. 1.

A plurality of projection units 110 may be disposed. In one embodiment, four projection units 110 may be disposed at equal sections at four positions around the circumference when viewed in a plan.

As described above, a plurality of the projection units 110 are arranged at predetermined positions, and each of the projection units 110 can irradiate the grid pattern light with a predetermined inclination angle toward the inspection target 10.

The illuminating unit 120 irradiates the inspection target 10 with at least two lights having different colors to obtain a color image of the inspection target 10.

In one embodiment, the illumination unit 120 may include a first illumination unit 122, a second illumination unit 124, and a third illumination unit 126.

For example, the first illumination unit 122 may irradiate the inspection target 10 with the first color light with a second inclination angle a2, the second illumination unit 124 may irradiate the inspection target 10 with the second color light with a third inclination angle a3, and the third illuminating unit 126 may irradiate the inspection target 10 with the third color light with a fourth inclination angle a4.

Here, the second inclination angle a2 is smaller than the first inclination angle a1 of the projection units 110, and the third inclination angle a3 and the fourth inclination angle a4 are greater than the first inclination angle a1 of the projection units 110. The first, second and third color lights have different colors from each other, and may have, for example, red, green and blue colors, respectively.

Each of the first illumination unit 122, the second illumination unit 124, and the third illumination unit 126 may have a ring shape. For example, LED lights may be continuously arranged, and generate monochromatic illumination.

Meanwhile, the first illuminating unit 122 may set the second inclination angle a2 to 0 degree or substantially 0 degree (for example, 0 degree to 10 degrees) so as to irradiate the inspection target 10 substantially vertically. In this case, the first illumination unit 122 may be coaxial illumination with respect to the image acquisition unit 130. In addition, the first illuminating unit 122 may not have a ring shape, and the first illuminating unit 122 may be disposed around the image acquisition unit 130, and may adopt a mirror or a beam splitter according to the suitability of the mechanical layout design for changing the optical path so that the light generated by the first illuminating unit 122 advances downward vertically. In this case, the inclination angle of the light emitted from the first illumination unit 122 can be set to 90 degrees or substantially 90 degrees (for example, 85 degrees to 95 degrees) with respect to a normal line perpendicular to the plane of the inspection target 10, and the second inclination angle a2 of light irradiated to the inspection target 10 via the mirror or the beam splitter is set to 0 degree or substantially 0 degree (for example, 0 degree to 10 degrees) as in is the case described above.

The image acquisition unit 130 acquires a first image by receiving light emitted from the projection unit 110 and reflected by the inspection target 10, and a second image by receiving light emitted from the illumination unit 120 and reflected by the inspection target 10. The image acquisition unit 130 may include, for example, a camera for image acquisition.

The image acquisition unit 130 may include at least one of the image acquisition units 130 to obtain the image in a vertical direction with respect to a plane of the inspection target 10 or in a tilted direction with respect to a normal line to the plane.

For example, each image acquisition unit 130 may include at least one camera in a direction perpendicular to a plane and at least one camera in a tilted state, thereby obtaining at least one first image and a second image.

The first image may include a grid pattern image generated by the grid pattern light, and three-dimensional shape information of the inspection target 10 can be obtained by applying a known bucket algorithm to a plurality of grid pattern images.

The second image is an image obtained using at least two color lights, and is a planar color image of the inspection target 10.

The processing unit 140 acquires brightness information from the first image acquired by the image acquisition unit 130 and acquires color information from the second image acquired by the image acquisition unit 130.

The first image obtained through the image acquisition unit 130 may be converted into a black-and-white image or a monochrome image through image processing. For example, if the first image is a grid pattern image, a monochrome image may be generated through image processing that averages a plurality of grid pattern images. Accordingly, the processing unit 140 may acquire brightness information from the first image. In this case, the first image can also be utilized for obtaining three-dimensional shape information by applying a scheme such as a well-known bucket algorithm. In addition, since the first image can be utilized for extracting brightness information as described above, efficient data utilization can be achieved.

The second image obtained through the image acquisition unit 110 includes color information since the second image is an image obtained using at least two color lights. Accordingly, the processing unit 140 can obtain color information from the second image.

The processing unit 140 acquires at least a portion of the boundaries of the terminals of the inspection target 10 by using the obtained brightness information and color information.

On the other hand, the brightness information and the color information means information on brightness and color (or hue) among hue, chroma (or saturation) and brightness, which are three attributes of a color. The hue, chroma, and brightness may be quantified for digital image processing. For example, the hue, chroma, and brightness may be expressed as HSI, HSV, HSL, and H indicates hue, and S indicates saturation. In addition, I, V, and L indicate brightness, which means intensity, value, and lightness, respectively.

The processing unit 140 may combine the first image and the second image to generate a composite image, and may obtain the brightness information and the color information from the composite image.

The processing unit 140 may be an apparatus capable of performing the above-described image processing, etc., and may include, for example, an embedded SW driver for performing corresponding image processing, a computer, etc. The processing unit 140 may control operations of the above-described components, that is, the projection units 110, the illumination unit 120, the image acquisition unit 130, etc.

Meanwhile, the processing unit 140 may obtain height data from the first image and modify the brightness data by using the height data. For example, the height data may include an image representing a height distribution, a distribution map representing a height distribution, a height value per position itself, and the like.

For example, when the processing unit 140 corrects the brightness information using the height data, the brightness information may be modified to a value of 0 when the height data is less than or equal to a reference height. That is, since a portion corresponding to the height below the predetermined reference height in the obtained brightness information is likely to be located outside the terminal region, such as the shadow region, the brightness information at this time may be set to zero.

The obtained brightness information may be, for example, one of intensity, value, and lightness, and may be modified to another form when the brightness information is modified. For example, when the obtained brightness information is intensity, the brightness information may be modified to a value form.

On the other hand, the image processing using the histogram can be utilized when correcting the above brightness information.

The processing unit 140 may acquire at least a portion of the boundaries of the terminal of the inspection target by using the modified brightness information and color information.

Hereinafter, a method for inspecting a terminal of a component 10 mounted on the substrate 20 by using the substrate inspecting apparatus 100 will be described in detail with reference to the drawings.

Figure 2:
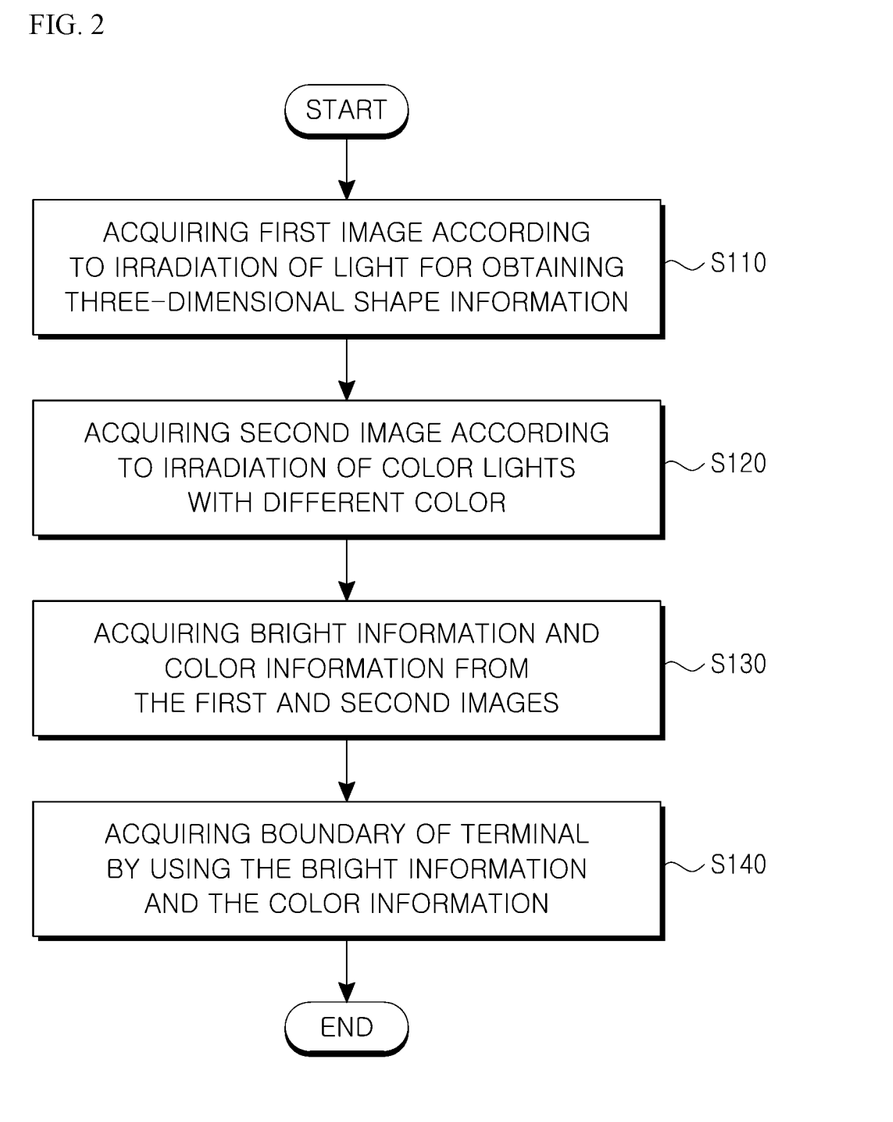
FIG. 2 is a flowchart showing a method of inspecting a terminal of a component according to an embodiment of the present invention.

FIG. 2 is a flowchart showing a method of inspecting a terminal of a component according to an embodiment of the present invention.

Referring to FIGS. 1 and 2, a first image according to irradiation of light for acquiring three-dimensional shape information is obtained (S110).

In one embodiment, the projection unit 110 may irradiate the inspection target 10 with grid pattern light for obtaining three-dimensional shape information of the inspection target 10, and the image acquisition unit 130 may receive the first image formed by grid pattern light reflected by the inspection target 10.

As described referring to FIG. 1, the light for obtaining the three-dimensional shape information of the inspection target 10 may be irradiated at a first inclination angle a1 with reference to a normal line perpendicular to the plane of the inspection target 10.

Subsequently, a second image is acquired according to the irradiation of the different color lights (S120).

In one embodiment, the illumination unit 120 may irradiate the inspection target 10 with at least two lights having different colors, and the image acquisition unit 130 may acquire the second image formed by the color lights reflected by the inspection target 10.

As described referring to FIG. 1, the lights may include first color light, second color light, and third color light of different colors. The first color light may be irradiated with the second inclination angle a2 smaller than the first inclination angle a1, and the second color light and the third color light may be irradiated with the third inclination angle a3 and the fourth inclination angle a4 larger than the first inclination angle a1. In one embodiment, the first, second, and third color lights are red light, green light, and blue light, respectively.

Meanwhile, the process of acquiring the first image (S110) and the process of acquiring the second image (S120) are not limited to the order. Thus, the first image may be acquired after acquiring the second image, and a plurality of first images and a plurality of second images may alternately be acquired.

Next, brightness the information and the color information are respectively obtained from the first and second images (S130).

At this time, the first image and the second image may be combined to generate a composite image, and then the brightness information and the color information may be obtained from the composite image.

On the other hand, the first and second images or the composite image obtained as described above can be subjected to predetermined image processing to easily and accurately acquire the image brightness information and the color information. For example, the brightness information may be enhanced or modified by assigning a height value to a height equal to or higher than a predetermined reference height and by setting zero to a height lower than the predetermined reference height in the black-and-white image generated by averaging the first image or the first images. In addition, the color information may be enhanced by assigning weights to R, G, and B values or H, S, and V values shown in the second image or the composite image.

Subsequently, at least a portion of the terminal boundary is obtained by using the obtained brightness information and the color information (S140).

The process of acquiring brightness information and color information (S130) and acquiring at least a portion of the terminal boundary (S140) may be performed by the processing unit 140 as described above.

Figure 3:
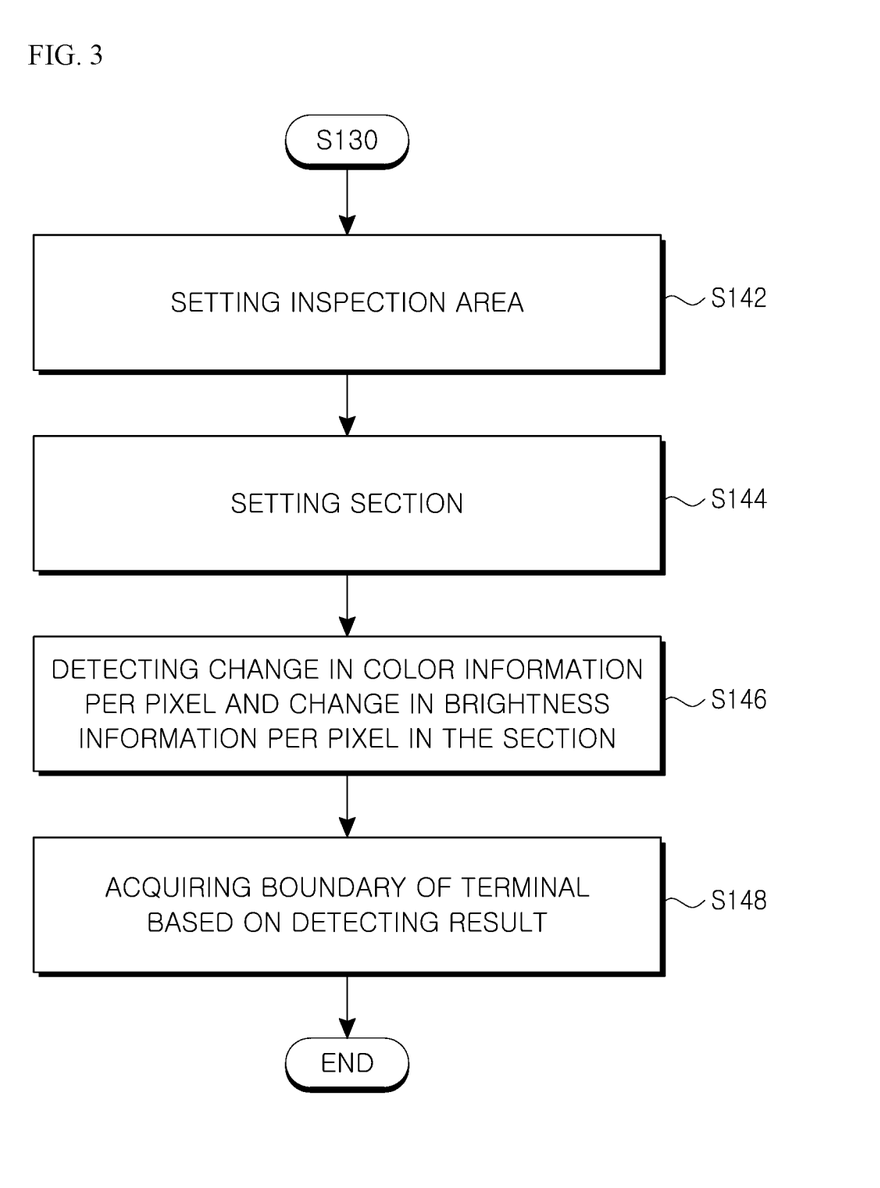
FIG. 3 is a flowchart showing an embodiment of a process for obtaining a terminal boundary in FIG. 2.
Figure 4:
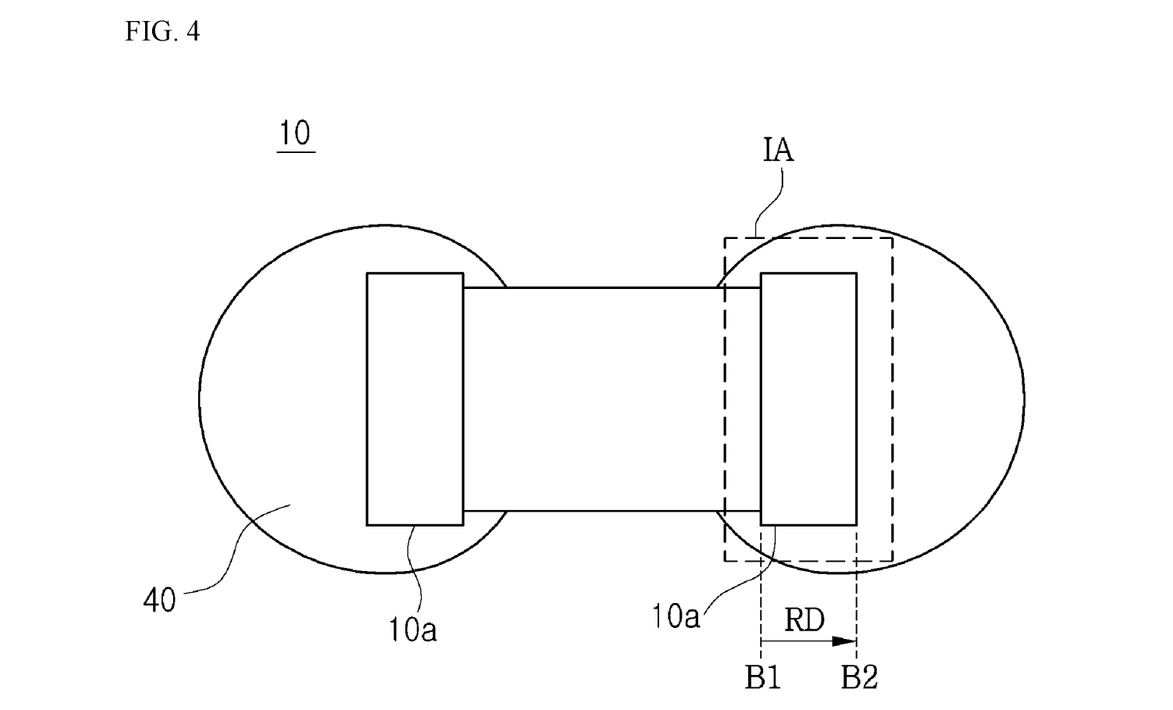
FIG. 4 is a conceptual diagram for explaining a process of acquiring a terminal boundary in FIG. 3.

FIG. 3 is a flowchart showing an embodiment of a process for obtaining a terminal boundary in FIG. 2. FIG. 4 is a conceptual diagram for explaining a process of acquiring a terminal boundary in FIG. 3.

Referring to FIGS. 1, 3 and 4, an inspection area IA is set on a composite image of the first and second images (S142).

The inspection area IA is set to include the terminal 10a of the component, which is the inspection target 10.

Subsequently, a section, in which the first color is changed to other color in the color of pixels, is set along a direction RD (hereinafter, referred to as 'reference direction') from the one side border B1 of the terminal toward the other side border B2 within the inspection area IA (S144).

Figure 5:
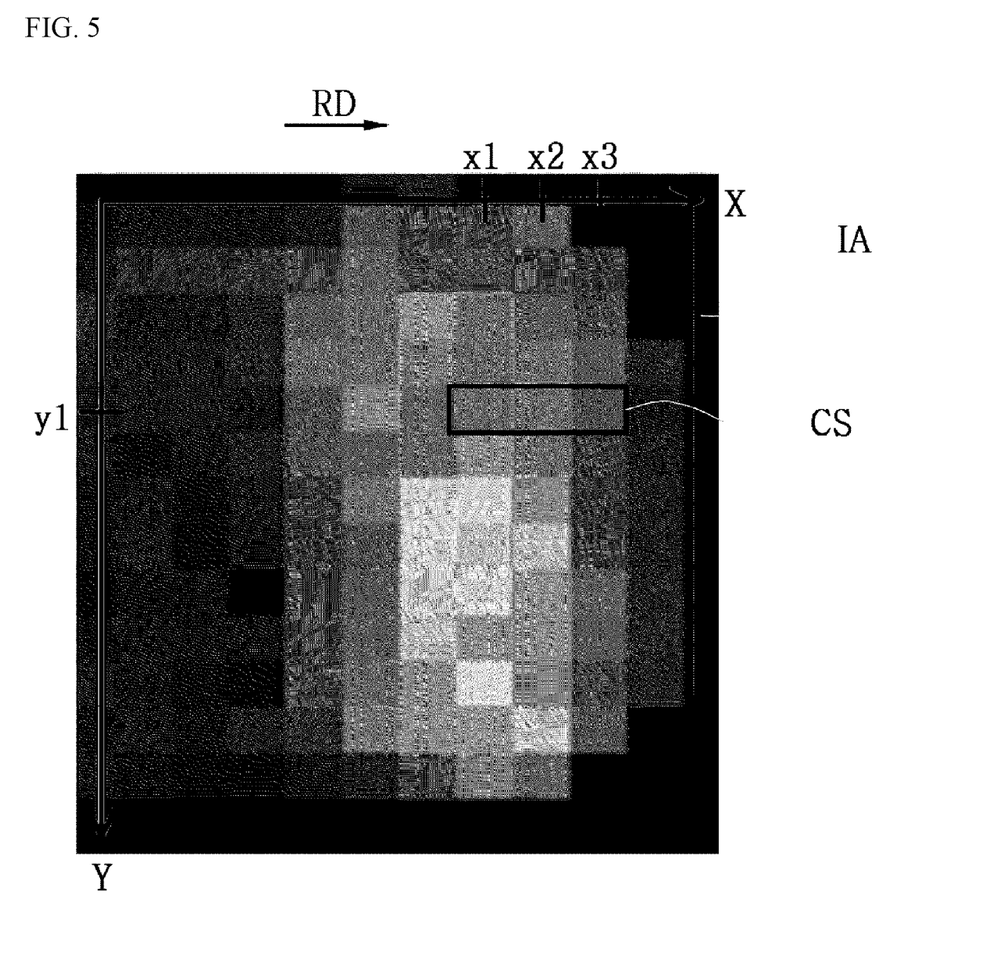
FIG. 5 is an image showing a composite image of the inspection area shown in FIG. 4.
Figure 6:
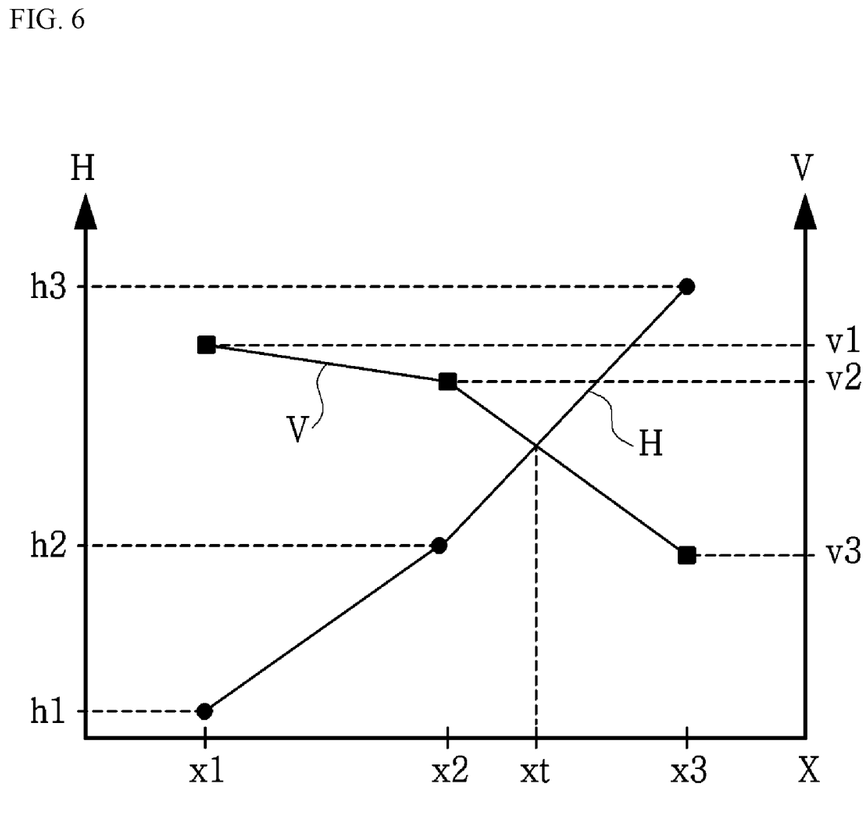
FIG. 6 is a graph showing changes in color and brightness in the section shown in FIG. 5.

FIG. 5 is an image showing a composite image of the inspection area shown in FIG. 4, and FIG. 6 is a graph showing changes in color and brightness in the section shown in FIG. 5.

Referring to FIGS. 5 and 6, it is possible to set a section CS in which a red color corresponding to the first color changes to a different color in one line in the inspection area IA. For example, when defining the coordinate system (XY) of an image as shown in FIG. 5, a section where a red color changes to another color in a pixel line corresponding to Y=y1 is X=x1, X=x2, X=x3.

Referring again to FIGS. 1, 3 and 4, a change in color information per pixel and a change in brightness information per pixel in the section are detected (S146). The change of the hue and the change of the brightness may be respectively a change of the hue value of each pixel and a change of the brightness value of each pixel according to the reference direction RD.

The hue and brightness may be set to a normalized quantitative value for each pixel. For example, as described in FIG. 1, hue, brightness, and saturation may be expressed as HSI, HSV, HSL, and the like. In one embodiment, it is quantified by using HSV in FIG. 6, where the hue is quantified as H (hue) and the lightness is quantified as V (value).

Subsequently, at least a portion of the boundaries of the terminal are acquired based on the change of the per-pixel color information and the per-pixel brightness information (S148).

Figure 7:
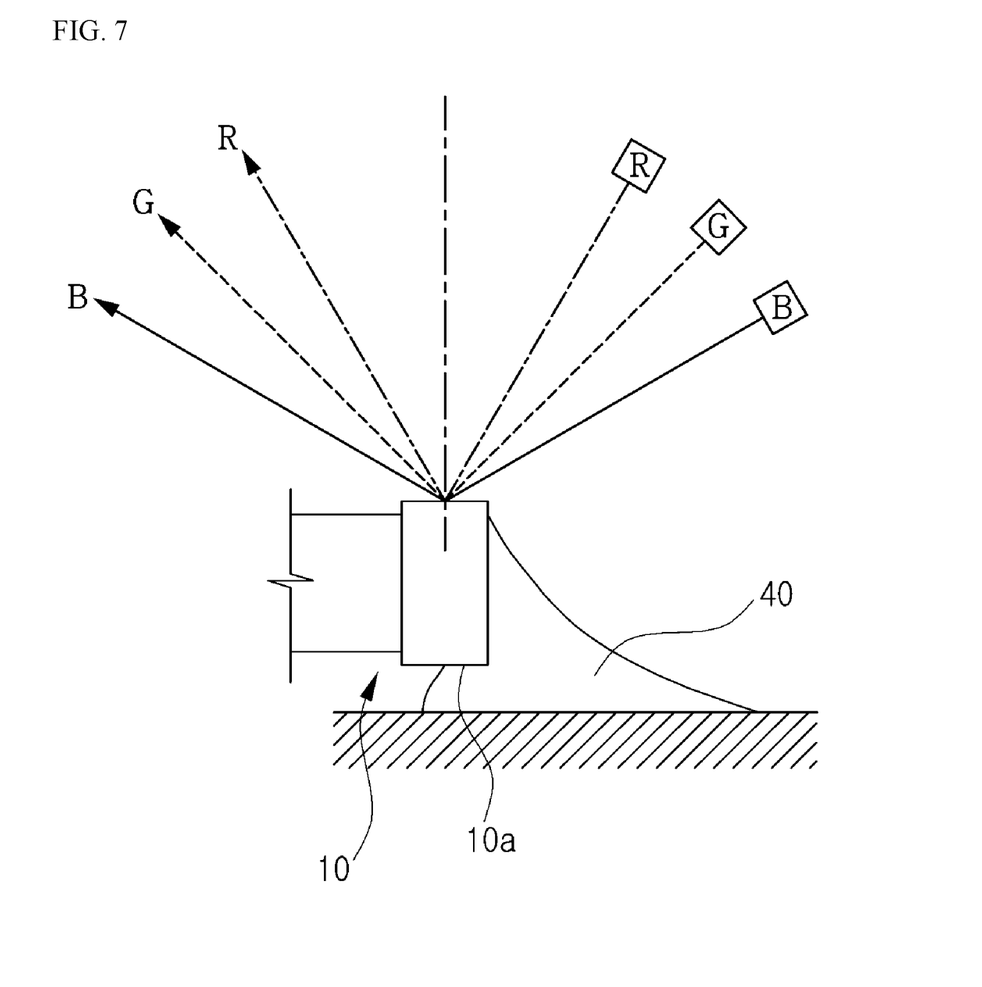
FIGS. 7 and 8 are conceptual diagrams for explaining a change in color per pixel and a change in brightness per pixel in FIGS. 5 and 6.
Figure 8:
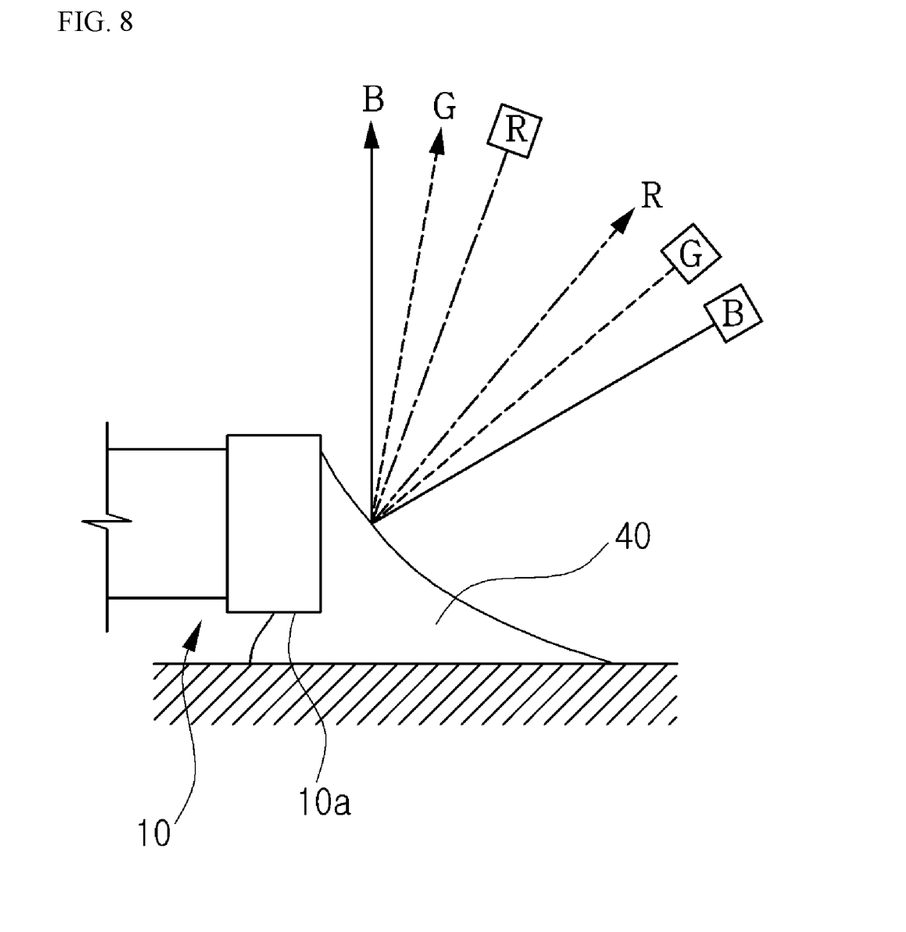

FIGS. 7 and 8 are conceptual diagrams for explaining a change in color per pixel and a change in brightness per pixel in FIGS. 5 and 6.

Referring to FIGS. 1 and 7, in the case of the terminal 10a of the component, light irradiated with a relatively small inclination angle with reference to a normal line perpendicular to the plane of the inspection target 10 is incident on the image acquisition unit 130 in relatively large amount, and light irradiated with a relatively large inclination angle with reference to the normal line is incident of the image acquisition unit 130 in relatively small amount. Accordingly, the first color light emitted from the first illuminating unit 122, which is illuminated with the largest inclination angle in the illuminating unit 120, is incident on the image acquisition unit 130 in most amount.

On the other hand, referring to FIGS. 1 and 8, in the case of the solder 40 formed adjacent to the terminal 10a of the component, light irradiated with a relatively small inclination angle with respect to the normal line perpendicular to the plane of the inspection target 10 is incident on the image acquisition unit 130 in relatively small amount, and light irradiated with a relatively large inclination angle is incident on the image acquisition unit 130 in relatively large amount. Accordingly, the first color light emitted from the first illumination unit 122 of the illumination unit 120 is incident on the image acquisition unit 130 in least amount.

In this manner, a sudden change in hue may occur at the terminal end which is the boundary of the terminal 10a of the component. Therefore, a point where the first color of the first color light irradiated to the inspection target 10 with the smallest inclination angle suddenly changes on the second image can be regarded as the terminal end.

On the other hand, the plurality of color lights of the illumination unit 120 may not be detected as desired due to scattering of light, and each color in the second image may not be clearly distinguished due to lack of light amount. Therefore, it may be difficult to determine the terminal end of the component by only changing the hue, and the result may also be inaccurate.

The first image acquired by the projection unit 110 can compensate for this problem.

The converted image of the first image or the first image by the projection unit 110 for obtaining the three-dimensional shape information of the inspection target 10 appears bright at the terminal 10a of the component and dark at a periphery according to the height.

For example, as described referring to FIG. 1, the projection unit 110 may irradiate the grid pattern light toward the inspection target 10 with a predetermined inclination angle, and the first image obtained by the image acquisition unit 130 may be converted into a black-and-white image or monochromatic image through image processing. Since the image processed and converted as described above appears bright at the terminal 10a of the component and appears dark at the periphery according to the height, the point where the sudden change from the high brightness portion to the low brightness portion in the converted image may be regarded as the terminal end.

Therefore, at least a portion of the boundary of the terminal 10a of the component such as the terminal end can be determined by utilizing the change in the brightness information in addition to the change in the color information described above.

Referring again to FIGS. 5 and 6, for example, when the first color is red, the hue increases along the reference direction RD and the brightness value decreases along the reference direction RD in the section CS set in a line in the inspection area IA.

In detail, in the section CS, the pixel-by-pixel color is represented by H=h1 at X=x1 and increases to H=h2 and H=h3 at X=x2 and X=x3, and the pixel-by-pixel brightness is represented by V=v1 at X=x1 and decreases to V=v2 and V=v3 at X=x2 and X=x3.

The intersection point of these two graphs is formed at X=xt. Considering both the change of the color information and the change of the brightness information, the intersection can be estimated as the terminal end of the component.

As described above, the terminal end, which is the boundary of the terminal 10a, can be determined as a point where an increasing trend line corresponding to a change in color value per pixel and a decreasing trend line corresponding to a change in brightness value per pixel meet each other. Thus, the boundary of a terminal of a component can be found in sub-pixel units, and a boundary of a terminal of a more accurate component can be obtained even when the size of the component is small.

On the other hand, the terminal ends can be determined on a line-by-line basis, that is, a Y coordinate on the XY coordinate system of FIG. 5, and the boundaries of the terminal ends can be determined by using the determined terminal ends. In this case, the terminal ends according to the Y coordinate can be obtained by using a method such as a least squares method.

It is possible to check whether the terminal of the component is defective by using the boundary of the terminal of the component determined as described above.

Meanwhile, the method of inspecting a terminal of a component may further include obtaining height data from the first image and correcting the brightness information using the height data. For example, the height data may include an image representing a height distribution, a distribution map representing a height distribution, a height value per position itself, and the like.

For example, in the step of modifying the brightness information by using the height data, the brightness information may be modified to a value of zero when the height data is less than or equal to a reference height. That is, since the portion corresponding to the height below the predetermined reference height in the obtained brightness information is likely to be located outside the terminal region, such as the shadow region, the brightness information at this time may be set to zero.

Further, the obtained brightness information may be, for example, one of intensity, value, and lightness, and may be modified to another form when the brightness information is modified. For example, when the obtained brightness information is intensity, the brightness information may be modified to a value form.

On the other hand, the image processing using the histogram can be utilized when correcting the above brightness information.

Accordingly, the step (S140) of acquiring at least a portion of the terminal boundary using the obtained brightness information and the color information may be performed by using the modified brightness information and the modified color information.

According to the method of inspecting a terminal of a component and the substrate inspection apparatus described above, a boundary of a terminal of the inspection target is acquired by using the bright information and the color information respectively obtained from the image for measuring three-dimensional shape and the color image to secure high accuracy and reliability, thereby improving the accuracy and reliability of inspection.

In addition, the terminal boundary of the inspection target can be obtained from data obtained by quantifying the brightness information and the color information pixel by pixel, the terminal boundary of the component can be detected in sub-pixel unit by determining the terminal end as an intersection of the graph obtained according to the change of the color value of each pixel, and the graph obtained according to the change of the brightness of each pixel, and the boundary of the terminal of the component can be obtained more accurately even when the size of the parts is small.

In addition, not only can three-dimensional shape information be acquired from an image for acquiring three-dimensional shape information of an inspection target, but also utilized for extraction of brightness information, efficient data utilization can be achieved.

Although the present invention has been described in the detailed description of the invention with reference to exemplary embodiments of the present invention, it will be understood to those skilled in the art that various modifications and variation can be made in the present invention without departing from the spirit or scope of the invention.

The invention claimed is:

1. A method of inspecting a terminal of a component, comprising:
   acquiring a first image by irradiating an inspection target with light for obtaining a three-dimensional image of the inspection target and receiving the light reflected by the inspection target, and a second image by irradiating the inspection target with at least two lights with different colors and receiving the at least two lights reflected by the inspection target;
   acquiring brightness information from the first image, and color information from the second image;
   producing a composite image of the first image and the second image by using the brightness information and the color information;
   setting an inspection area including a terminal of the inspection target in the composite image;
   detecting a change in color information per pixel and a change in brightness information per pixel in the inspection area; and
   discriminating a terminal area and a solder area based on the change of the color information per pixel and the change of the brightness information per pixel on the composite image.

2. The method of claim 1, wherein the light for obtaining three-dimensional image of the inspection target is irradiated with a first inclination angle with reference to a normal line perpendicular to the plane of the inspection target, and
   the at least two lights with different colors include at least a first color light and a second color light having a different color from the first color light, the first color light is irradiated with a second inclination angle smaller than the first inclination angle, and the second color light is irradiated with a third inclination angle larger than the first inclination angle.

3. A method of inspecting a terminal of a component, comprising:
   acquiring a first image by irradiating an inspection target with light for obtaining a three-dimensional image of the inspection target and receiving the light reflected by the inspection target, and a second image by irradiating the inspection target with at least two lights with different colors and receiving the at least two lights reflected by the inspection target;
   acquiring brightness information from the first image, and color information from the second image; and
   acquiring at least a portion of a boundary of the terminal of the inspection target by using the brightness information and the color information,
   wherein the light for obtaining the three-dimensional image of the inspection target is irradiated with a first inclination angle with reference to a normal line perpendicular to the plane of the inspection target, and the at least two lights with different colors include at least a first color light and a second color light having a different color from the first color light, the first color light is irradiated with a second inclination angle smaller than the first inclination angle, and the second color light is irradiated with a third inclination angle larger than the first inclination angle, wherein acquiring at least a portion of a boundary of the terminal of the inspection target by using the brightness information and the color information, comprises:

setting an inspection area including a terminal of the inspection target in a composite image of the first and second images;

setting a section in which the color of a pixel changes from the first color to another color along a direction from one side boundary of the terminal to other side boundary (hereinafter referred to as 'reference direction') within the inspection area;

detecting a change in color information per pixel and a change in brightness information per pixel in the section; and obtaining at least a portion of the boundaries of the terminal, based on the change of the color information per pixel and the change of the brightness information per pixel.

4. The method of claim 3, wherein the color and the brightness are set to a normalized quantitative value for each pixel, and the change of the color and the change of the brightness are respectively a change of a color value per pixel and a change of a brightness value per pixel according to the reference direction.

5. The method of claim 4, wherein the first color is red, the change of the color is increased in the section according to the reference direction and the change of the brightness is decreased in the section according to the reference direction, and wherein the boundary of the terminal is determined by a point where an increasing trend line corresponding to the change of the color value per pixel meets a decreasing trend line corresponding to the change of the brightness value per pixel.

6. The method of claim 1, further comprising:
obtaining height data from the first image; and
modifying the brightness information by using the height data,
wherein acquiring at least a portion of a boundary of the terminal of the inspection target, is performed by using the modified brightness information and the color information.

7. The method of claim 6, wherein modifying the brightness information by using the height data is performed by setting the brightness information to zero when the height data is less than or equal to a reference height.

8. A substrate inspection apparatus comprising:
a projection unit irradiating an inspection target with light for obtaining three-dimensional shape information of the inspection target;
an illumination unit irradiating the inspection target with at least two lights having different colors;
an image acquisition unit acquiring a first image by receiving light irradiated by the projection unit and reflected from the inspection target, and a second image by receiving the lights irradiated by the illumination unit and reflected from the inspection target; and
a processing unit acquiring brightness information and color information from the first image and the second image, respectively, which are acquired by the image acquisition unit, and
producing a composite image of the first image and the second image by using the brightness information and the color information,
setting an inspection area including a terminal of the inspection target in the composite image;
detecting a change in color information per pixel and a change in brightness information per pixel in the inspection area; and
discriminating a terminal area and a solder area based on the change of the color information per pixel and the change of the brightness information per pixel on the composite image.

9. The substrate inspection apparatus of claim 8, wherein at least one projection unit is disposed, and irradiates the inspection target with light for obtaining three-dimensional shape information with a first inclination angle with respect to a normal line perpendicular to a plane of the inspection target, and the lighting unit comprises:
a first illumination unit irradiating the inspection target with a first color light having a first color with a second inclination angle smaller than the first inclination angle of the projection unit; and
a second illumination unit irradiating the inspection target with a second color light having a second color different from the first color with a third inclination angle larger than the first inclination angle of the projection unit.

10. A substrate inspection apparatus comprising:
a projection unit irradiating an inspection target with light for obtaining three-dimensional shape information of the inspection target;
an illumination unit irradiating the inspection target with at least two lights having different colors;
an image acquisition unit acquiring a first image by receiving light irradiated by the projection unit and reflected from the inspection target, and a second image by receiving the lights irradiated by the illumination unit and reflected from the inspection target; and
a processing unit acquiring brightness information and color information from the first image and the second image, respectively, which are acquired by the image acquisition unit, and acquiring at least a portion of a boundary by using the brightness information and the color information,
wherein at least one projection unit is disposed, and irradiates the inspection target with light for obtaining three-dimensional shape information with a first inclination angle with respect to a normal line perpendicular to a plane of the inspection target, and the lighting unit comprises:
a first illumination unit irradiating the inspection target with a first color light having a first color with a second inclination angle smaller than the first inclination angle of the projection unit; and
a second illumination unit irradiating the inspection target with a second color light having a second color different from the first color with a third inclination angle larger than the first inclination angle of the projection unit, wherein the processing unit sets a section in which the color of a pixel changes from the first color to another color along a direction from one side boundary of the terminal to other side boundary (hereinafter referred to as 'reference direction') within an inspection area in the composite image of the first and second images, which includes the terminal of the inspection target, and acquires at least a portion of a boundary of the terminal, based on a change of the color information per pixel and a change of the brightness information per pixel in the section.

11. The substrate inspection apparatus of claim 10, wherein the color and the brightness are set to a normalized quantitative value for each pixel, and the change of the color and the change of the brightness are respectively a change of a color value per pixel and a change of a brightness value per pixel according to the reference direction.

12. The substrate inspection apparatus of claim 11, wherein the first color is red, the change of the color is increased in the section according to the reference direction and the change of the brightness is decreased in the section according to the reference direction, and wherein the boundary of the terminal is determined by a point where an increasing trend line corresponding to the change of the color value per pixel meets a decreasing trend line corresponding to the change of the brightness value per pixel.

13. The substrate inspection apparatus of claim 8, wherein the processing unit acquires height data from the first image, modifies the brightness information by using the height data, and acquires at least a portion of the boundaries of the terminal of the inspection target by using the modified brightness information and the color information.

14. The substrate inspection apparatus of claim 13, wherein the processing unit sets the brightness information to zero, when the height data is less than or equal to a reference height in modifying the brightness data by using the height data.

* * * * *